United States Patent
Hengstenberg et al.

(10) Patent No.: US 7,811,247 B2
(45) Date of Patent: Oct. 12, 2010

(54) METHOD AND ARRANGEMENT FOR MONITORING AN ADMINISTRATION OF AT LEAST ONE MEDICATION

(75) Inventors: Andreas Hengstenberg, Reinfeld (DE); Götz Kullik, Lübeck (DE)

(73) Assignee: Draeger Medical AG & Co. KG, Luebeck (DE)

( * ) Notice: Subject to any disclaimer, the term of this patent is extended or adjusted under 35 U.S.C. 154(b) by 142 days.

(21) Appl. No.: 11/902,538

(22) Filed: Sep. 24, 2007

(65) Prior Publication Data

US 2008/0077080 A1  Mar. 27, 2008

(30) Foreign Application Priority Data

Sep. 23, 2006  (DE)  ........................ 10 2006 045 014

(51) Int. Cl.
*A61M 31/00* (2006.01)
(52) U.S. Cl. ...................................................... 604/66
(58) Field of Classification Search .................... 604/66
See application file for complete search history.

(56) References Cited

U.S. PATENT DOCUMENTS

| | | | | |
|---|---|---|---|---|
| 5,813,993 A | * | 9/1998 | Kaplan et al. | 600/544 |
| 5,875,783 A | * | 3/1999 | Kullik | 128/204.18 |
| 6,622,725 B1 | * | 9/2003 | Fisher et al. | 128/204.21 |
| 6,981,947 B2 | * | 1/2006 | Melker | 600/532 |
| 2002/0173729 A1 | * | 11/2002 | Viertio-Oja et al. | 600/544 |
| 2005/0022811 A1 | * | 2/2005 | Kiesele et al. | 128/203.12 |
| 2007/0282251 A1 | * | 12/2007 | Barvais et al. | 604/67 |

FOREIGN PATENT DOCUMENTS

WO  WO 2004/030525  4/2004

* cited by examiner

*Primary Examiner*—Nicholas D Lucchesi
*Assistant Examiner*—Diva Ranade
(74) *Attorney, Agent, or Firm*—Walter Ottesen

(57) ABSTRACT

An arrangement is provided for monitoring a metering of at least one medication administered to a patient. The concentration of the active ingredient of the medication, which is measured in the breathing gas of a patient, is balanced with a computed concentration in the breathing gas. When a change of the administered quantity of the medication takes place, the concentration range (13) is adapted. The concentration, which is measured in the breathing gas, must lie by computation within this range. An arrangement for administering at least one medication and a method for monitoring a metering or dosing of the medication as well as a method for treating a patient are provided.

9 Claims, 4 Drawing Sheets

METHOD AND ARRANGEMENT FOR MONITORING AN ADMINISTRATION OF AT LEAST ONE MEDICATION

CROSS REFERENCE TO RELATED APPLICATION

This application claims priority of German patent application no. 10 2006 045 014.0, filed Sep. 23, 2006, the entire content of which is incorporated herein by reference.

FIELD OF THE INVENTION

The invention relates to an arrangement for monitoring a dosing of at least one medication administered to a patient and an apparatus for dosing at least one medication. The invention also relates to a method for monitoring a dosing of a medication administered to a patient.

BACKGROUND OF THE INVENTION

Medications are known which, with the same dosage, lead to differently high active substance levels between different persons as well as between different types of mammals. This leads to difficulties in the administration of such a medication when the medication has, at the same time, a narrow therapeutic effective range so that even a comparatively small overdosage or underdosage leads to an intoxication or a loss of the therapeutic effect of the medication.

An example of such a medication is the intravenously administered propofol. Propofol is an anesthetic and sedative which can have grave side effects such as respiratory depression, apnea and a drop in blood pressure with the danger of shock when dosages are too high; however, in the case where the dosage is too low, an awakening of the patient from anesthesia can no longer be reliably prevented. As a rule, propofol is often used together with muscular relaxants for anesthesia. For this reason, an underdosage leads to an awakening of the patient, however, because of the relaxed state of the patient, the patient cannot express this; instead, the patient experiences the further course of the surgical procedure in a state of awakeness which the patient cannot indicate to the attending physicians. While the patient experiences unavoidably the discomfort caused by the surgical procedure, there remains for the patient only the hope that the anesthetist sooner or later recognizes his awakening out of the anesthesia and rapidly reacts correspondingly.

It is true that, for this purpose, the anesthetist has monitors, which are known to the state of the art, for monitoring the depth of anesthesia of a patient and therewith for monitoring the concentration of propofol as described, for example, in U.S. Pat. No. 6,981,947. As described in this patent, the plasma concentration of an intravenously administered medication such as propofol can be determined based on the measurements of breathing gas or can at least be estimated. The anesthetist can therefore be alerted as soon as the concentration of propofol, which is determined in the breathing gas, exceeds or drops below a previously determined concentration range.

This procedure is, however, subjected to disadvantages because the anesthetist, as a rule, only learns of, for example, technical errors when the breathing gas concentration moves out of the determined range. These technical errors can be: malfunctions of a perfuser with which the medication is administered; blocking of a venous access; disturbances of infusion lines or accessories; leakages of such infusions lines or accessories; dislocation of infusion canulas; inadvertent mix-ups of medications; typing errors; defective computations and the like. It can then, however, already be too late to alleviate the technical problems or to increase the dosage of propofol before the patient awakens. It is true that the anesthetist can set the limits of the concentration range as narrow as desired with a warning announcement resulting when there is a movement out of this concentration range. However, the tighter the limits are made, the more often there are false alarms.

These problems occur not only with the above-described intravenous administration of propofol but also during administration of other medications and also when administering the medications via other accesses such as intraarterially, intraperitoneally, intramuscularly, subcutaneously, topically, orally or as inhalant.

SUMMARY OF THE INVENTION

In view of the above, it is an object of the invention to provide arrangements and methods for monitoring the dosing of medications and for administering the medications which lead to a higher safety and reliability in the monitoring of the dosing and the administration of the medication.

The arrangement of the invention is for monitoring a dosing of a medication administered to a patient. The arrangement includes: a device for measuring the concentration of the medication in the breathing gas of the patient; an evaluation unit for detecting a deviation of the measured concentration of the medication from a pregiven concentration range; a unit for providing information about the quantity of the medication delivered to the patient; and, a device for determining the pregiven concentration range based on the quantity of medication delivered.

According to the invention, an arrangement for monitoring a dosing of at least one medication administered to a patient is suggested. The arrangement includes means for measuring the concentration of at least one active substance of a medication in the breathing gas and at least one evaluation unit for detecting a deviation of the concentration of the active substance, which is measured in the breathing gas, from a concentration range.

In this context, it is noted that, in the following, the term "patient" can be a person or any other mammal. The term "medication" is, according to the invention, understood to be any substance which is administered to or is ingested by the patient, for example, for the purpose of therapy or diagnosis. The term "active substance" can, according to the invention, be a medically effective substance which is contained in the medication. The medication can contain more than only one active substance and, on the other hand, the medication can consist of only the active substance. The term "active substance" is, according to the invention, also any metabolized form of a substance contained in the medication which can be measured in the breathing gas of the patient and the measurement of which permits conclusions to be drawn as to a blood concentration of at least this or at least one other active substance. Accordingly, a multiplicity of chemical substances, which are, for example, generated by metabolic occurrences, are likewise active substances in the sense of the invention described herein. According to the invention, it is also provided that proportions of active substances are measured. It is here insignificant whether this substance is gaseous, solid or is present in other states. The term "breathing gas" is understood to be that gas mixture which the patient exhales. Depending upon the area of application, it is, however, up to the person of skill in this art whether the concentration of the active substance is measured in the expiratory breathing gas of the patient or, at steady-state conditions or during reinhaling expiratory breathing gas, in the inspiratory breathing gas of the patient or whether the measurement is conducted in sections of the apparatus which are in gas connection with the lungs and which are not assignable exclusively to the inspiratory or expiratory region of this apparatus.

The means for measuring the concentration of the active substance or several active substances are known to the person working in the area of the invention. For example, means of this kind which are provided in accordance with the invention are disclosed in United States patent application publication US 2005/0022811 A1 incorporated herein by reference. U.S. Pat. No. 6,981,947 is also incorporated herein by reference and describes such means or provides suggestions with respect thereto where such means are described in the pertinent literature.

According to the invention, a determination is made with the evaluation unit for detecting a deviation of the concentration of the active substance measured in the breathing gas from a concentration range and it is determined whether the measured concentration exceeds or drops below previously determined upper and/or lower limits (so-called limit values) for the concentration of the particular active substance and therefore whether the concentration range is exceeded or there is a drop below this concentration range. The concentration range can be determined at the apparatus; however, as may be required, it can also be read in from memories or, for the individual case, be fixedly or variably set by the operator of the arrangement for monitoring the administering of the medication. In the context of the invention, there is not only a monitoring of limit values being exceeded but also an evaluation of the trend curve of the measured concentration and, if required, there is a corresponding adaptation of the dosage administered.

The arrangement for monitoring an administration of medication according to the invention further includes means for detecting the administered quantity of the medication as well as a unit for adapting the concentration range based on a change of the medication administered.

Because of the means for detecting the administered quantity of the medication, the quantity of the medication which is administered to the patient at the particular time point is detected continuously or at discrete time points. Especially with a medication delivery maintained over a specific time, it can also be purposeful according to the invention to detect only the concentration change when administering the medication with the means for detecting the administered concentration. Suitable apparatus are known for this purpose from the state of the art. A conventional example of such means for detecting the administered concentration are monitors, which display to the physician or attending personnel the concentration of a medication which is administered, for example, intravenously. The concentration is adjusted on a perfuser or on an injection pump.

The above-mentioned limits of the concentration range can be varied by means of the apparatus for adapting the concentration range based on a change of the administered quantity of the medication. When the attending physician increases, for example, the quantity of the medication administered by the perfuser, then the limits of the concentration range increase in correspondence to the newly adjusted concentration. False alarms are thereby advantageously avoided. In addition, purposeful alarms with corrected increased limit concentrations are made possible. The same applies to a reduction of the quantity of the administered medication by the physician.

The present invention is advantageous in that the user or the attendant when applying a medication receives a comparatively early announcement as to whether, after an increase of the dosage of the administered medication, a concentration increase actually takes place in the blood of the patient as shown by an increase of the concentration in the breathing air. In contrast to the procedure followed in the state of the art, this is made possible in that comparatively narrow limits for the concentration range can be drawn without the danger of false alarms as described in the above state of the art when limits are narrow. The basis for this is that the change of the limits can trigger an alarm when these limits are exceeded or there is a drop below these limits in correspondence to the undertaken change of the administered quantity of the medication. Stated otherwise, the information that the administered quantity is changed leads already to an adaptation of the concentration range. If the measured breathing gas concentration does not correspondingly change then it can be assumed that a technical fault is present. The operator of a metering or dosing apparatus, which is monitored by means of the arrangement of the invention, therefore recognizes very early that an increase of the quantity of the administered medication has not also led to an increase of the concentration in the blood or in the breathing gas. The reasons can lie, as described above, for example, in a malfunction of the utilized apparatus for administering the medication, a dislocation of the utilized venule or catheter and the like. The apparatus of the invention can at any desired fixed time points compare the breathing gas concentrations, which are to be expected because of the administered quantity or a change of the metered quantity, to the breathing gas concentrations detected by means of the device for detecting the concentration. For this reason, an alarm announcement can be outputted or, generally, this result can be communicated already at the first indication of a deviation between computed and actual breathing gas concentration.

Accordingly, the arrangement of the invention for monitoring a metering or dosing in accordance with a preferred embodiment has a unit for intravenously administering the medication. A further preferred embodiment includes a unit for communicating a deviation of the measured concentration range concentration out of the calculated concentration range as already mentioned above. This unit for communication can be a monitor, an optical and/or acoustic unit of any kind which informs and/or alarms.

In each of the above-described embodiments or feature combinations, methods and techniques as well as units suitable for carrying out these methods and techniques can be used or provided which permit a further evaluation of the blood concentration or plasma concentration of the administered medication. For this purpose, the following are pertinent: for example, the changes which are measured in an electroencephalogram (EEG), bispectralindex-monitoring (BIS) as well as acoustically evoked potentials and the like which permit conclusions to be drawn as to the depth of anesthesia after administration of an anesthetic.

In addition, in each of the above-described embodiments of the invention, the following can be provided: a unit for measuring a pressure increase in the infusion system as well as a method for measuring such a pressure increase or, generally, a pressure change by means of which, for example, a clogging within the infusion system can be detected.

In a further embodiment, additional data can be called up and/or stored which data are of assistance in a pharmacokinetic computation of the dosage, such as body weight, age, sex, body mass index and the like. A corresponding unit can be provided in accordance with the invention.

Furthermore, in a preferred embodiment, a method and a unit are provided by means of which fixed dosages are checked as to the plausibility thereof based on additional data and information such as age of the patient and patient weight. The inputted maximum values and minimum values for the active substance concentration in the breathing gas can also be checked herewith which leads to increased safety for the patient.

In a further embodiment of the invention, a specific dosage or infusion rate of the at least one medication is administered to the patient in advance of treatment with the at least one medication. This takes place, for example, for initiating an anesthesia (with propofol) in the form of a bolus injection. With pharmacokinetic computations, the blood concentration, which results from this dosage or infusion rate, can be continuously computed. After the elapse of a specific time duration, the computed blood concentration is brought into relationship with the concentration measured in the breathing gas. In this way, the individual blood/gas distribution ratio of the medication or its active substance is determined for an individual patient. With this relationship, an improved control of the treatment takes place with the medication based on the measurement of the at least one active substance in the breathing gas because now each concentration change in the breathing gas can be brought quantitatively into relationship with a change of the blood concentration or plasma concentration of the medication or of the active substance.

As indicated above, the present invention is not limited to a method and an arrangement for monitoring a metering or dosing in the context of an anesthesia and also not to the intravenous administration of propofol. The present invention also increases the safety in dealing with patients which are not ventilated. An application of the invention is, for example, also possible in a spontaneously breathing patient when taking samples of the breathing air via nose spectacles or a mask when propofol is used, for example, for sedating during a diagnostic procedure perceived as unpleasant. With each sampling of the breathing gas, especially in breathing circuits, it should be noted that no propofol-containing air is supplied to the patient in the inspiration branch because the inhaled propofol is again exhaled and conclusions as to the propofol concentration in the blood are made difficult or are falsified. To achieve this, a corresponding filter or absorber for propofol can be utilized. This filter is manufactured from suitable plastic materials.

The object of the invention is achieved also via an arrangement for administering at least one medication as well as a method for monitoring a metering or dosing of the medication. The object of the invention is further achieved via a method for treating a patient while using an arrangement for monitoring the metering and/or while using an apparatus for administering at least one medication.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
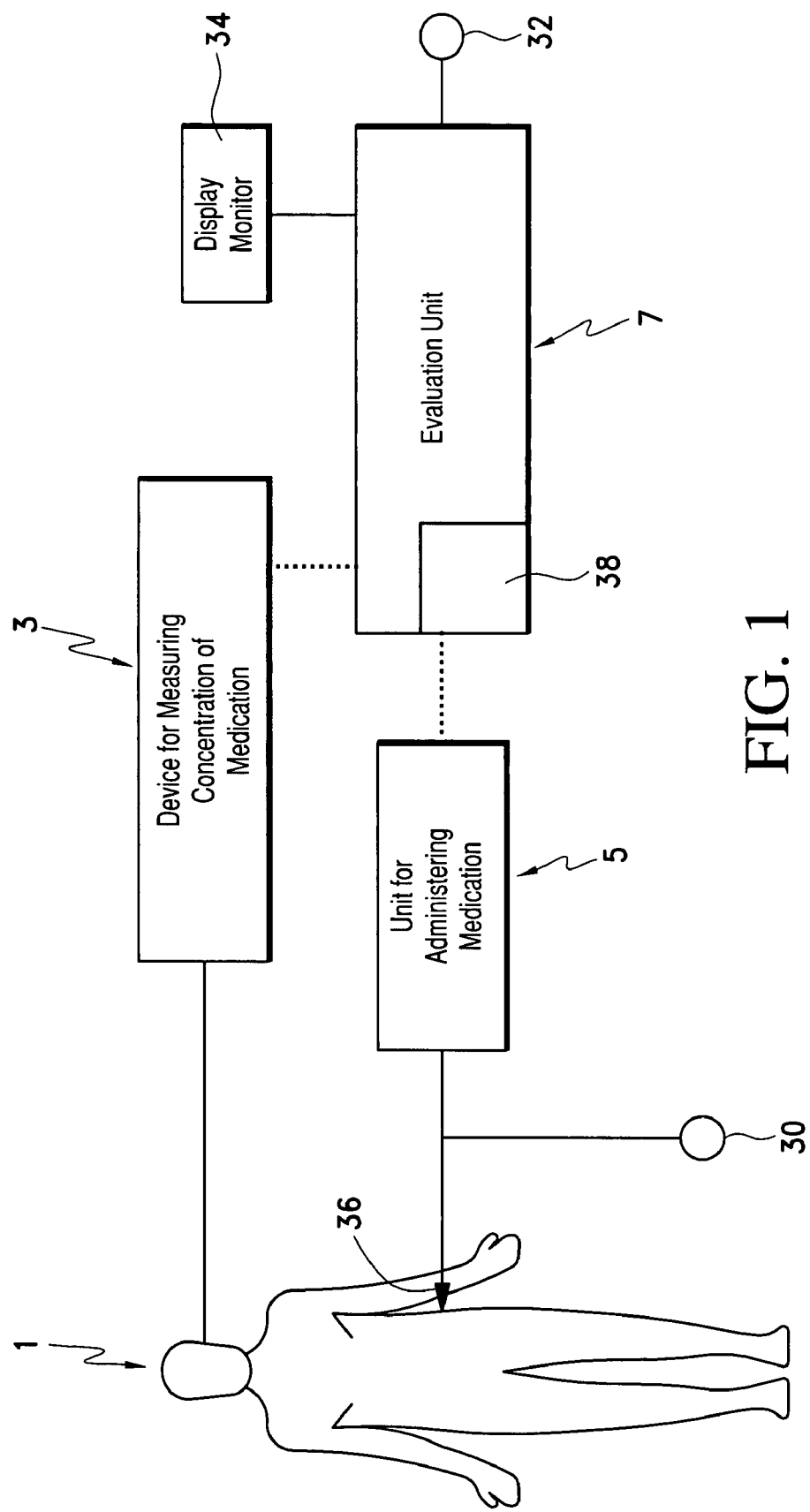
FIG. 1 is a schematic showing the arrangement of the invention for monitoring an administration of a medication.

FIG. 1 shows a patient 1 connected to a device 3 for measuring the concentration of an active substance of a medication. The device 3 measures the concentration of the medication or of the active substance in the breathing gas of the patient 1. A unit 5 for administering the medication is also connected to the patient 1. The unit 5 can, for example, be a perfuser, injection pump or the like.

The direct connection to the patient can be via device 36 for intravenously administering the medication to the patient. The information about the quantity of medication administered to the patient can be obtained from unit 5 or a measuring device 30 detects the quantity of medication delivered to the patient.

The dotted lines in FIG. 1 indicate that the device 3 for measuring the concentration and the unit 5 for administering the medication are connected to an evaluation unit 7. The evaluation unit 7 can have a warning unit which indicates when a computed concentration of the medication in the breathing gas does not match the value measured by means of the device 3.

Figure 2:
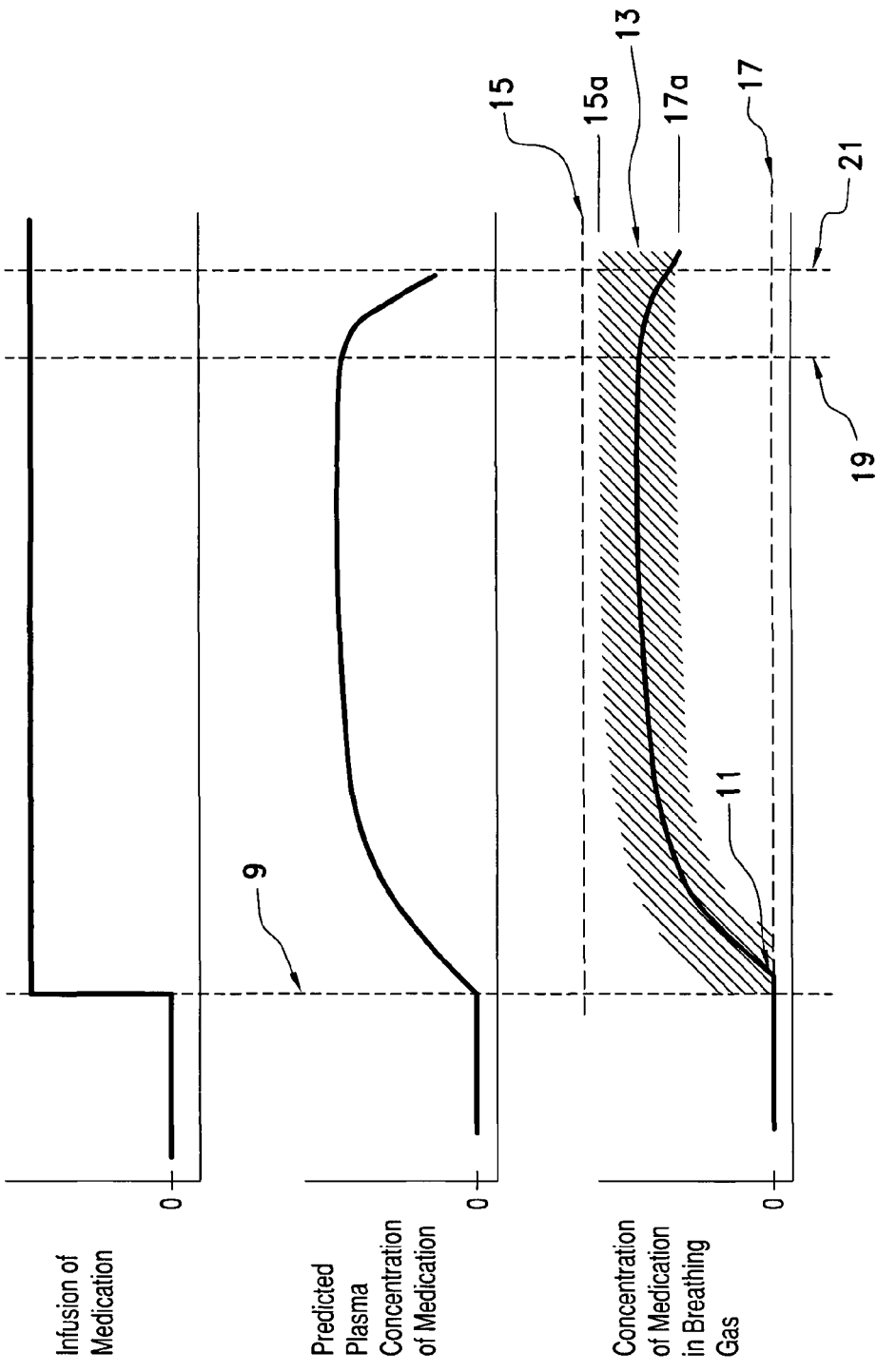
FIG. 2a is a graph showing the course of a rate of infusion.
FIG. 2b is a curve showing a plasma concentration of the medication as a function of time with the plasma concentration being predicted in accordance with a pharmacokinetic model.
FIG. 2c shows a measured breathing gas concentration, minimum and maximum thresholds and a prediction interval or concentration range with lower and upper limit values.

FIG. 2a shows the quantity of the medication as a function of time with the quantity being administered by the device 5 of FIG. 1.

FIG. 2b shows the plasma concentration of the active substance as a function of time and shows the increase of the plasma concentration of the measured active substance. This increase of plasma concentration takes place essentially simultaneously with the administration of the medication at a time point 9.

FIG. 2c is a graph showing a measured breathing gas concentration having minimum and maximum thresholds (17, 15) and a prediction interval or concentration range with lower and upper limit values (17a, 15a).

In FIG. 2c, time point 11 is after time point 9 in time. At time point 11, an increase of the concentration of the medication in the breathing gas takes place with FIG. 2c showing the breathing gas concentration as a function of time. In FIG. 2c, a concentration range 13 is shown by hatching. This concentration range 13 is the range in which the breathing gas concentration of the active substance should lie in accordance with expectation or in accordance with a computation or a pharmacokinetic model. In FIG. 2c, an upper, maximum threshold value 15 as well as a lower, minimum threshold value 17 are additionally indicated as they are known from the state of the art.

In the state of the art, an alarm (for example, when there is a falling breathing gas concentration) is outputted when there is a movement out of the concentration range, which lies between the threshold values 15 and 17, and a value below the threshold value 17 or above the threshold value 15 is measured. The concentration range lying between the threshold values 15 and 17 is adjusted by the apparatus or by the operator of the apparatus.

An advantage of the arrangement of the invention for monitoring the dosing or administering is especially clearly shown at time point 19 in FIGS. 2a to 2c. At time point 19, it should be assumed for reasons of the explanation of the invention that, because of a leak of the apparatus for administering the medication, the quantity of the medication outputted by the unit 5 for administering the medication remains constant but the medication is no longer administered to the patient and instead is lost for treatment and does not get into the blood of the patient as shown by the plasma concentration of FIG. 2b after time point 19. The breathing gas concentration also falls off after a time delay as can be seen in FIG. 2c.

The reason that the medication, which is outputted after time point 19, does not reach the blood of the patient is not based on a change intended by the physician and adjusted on the unit 5. Therefore, the dark hatched concentration range 13 remains unchanged after time point 19. The concentration value in the breathing gas (FIG. 2c) drops off in time spaced relationship to the plasma concentration of FIG. 2b. This concentration value drops below a lower limit value 17a of the concentration range 13 at a time point 21. Therefore, and in accordance with the invention, a warning can be outputted already at time point 21 which indicates the technical fault present already since time point 19. This alarm announcement thereby takes place significantly earlier than is the case in the state of the art. There, a drop below the threshold value 17 is necessary for obtaining an alarm signal. The evaluation unit 7 can be connected to units such as a display device 34 for communicating a deviation of the concentration out of the concentration range 13. The alarm announcement can be outputted via an acoustic alarm unit 32 connected to the evaluation unit 7.

Figure 3:
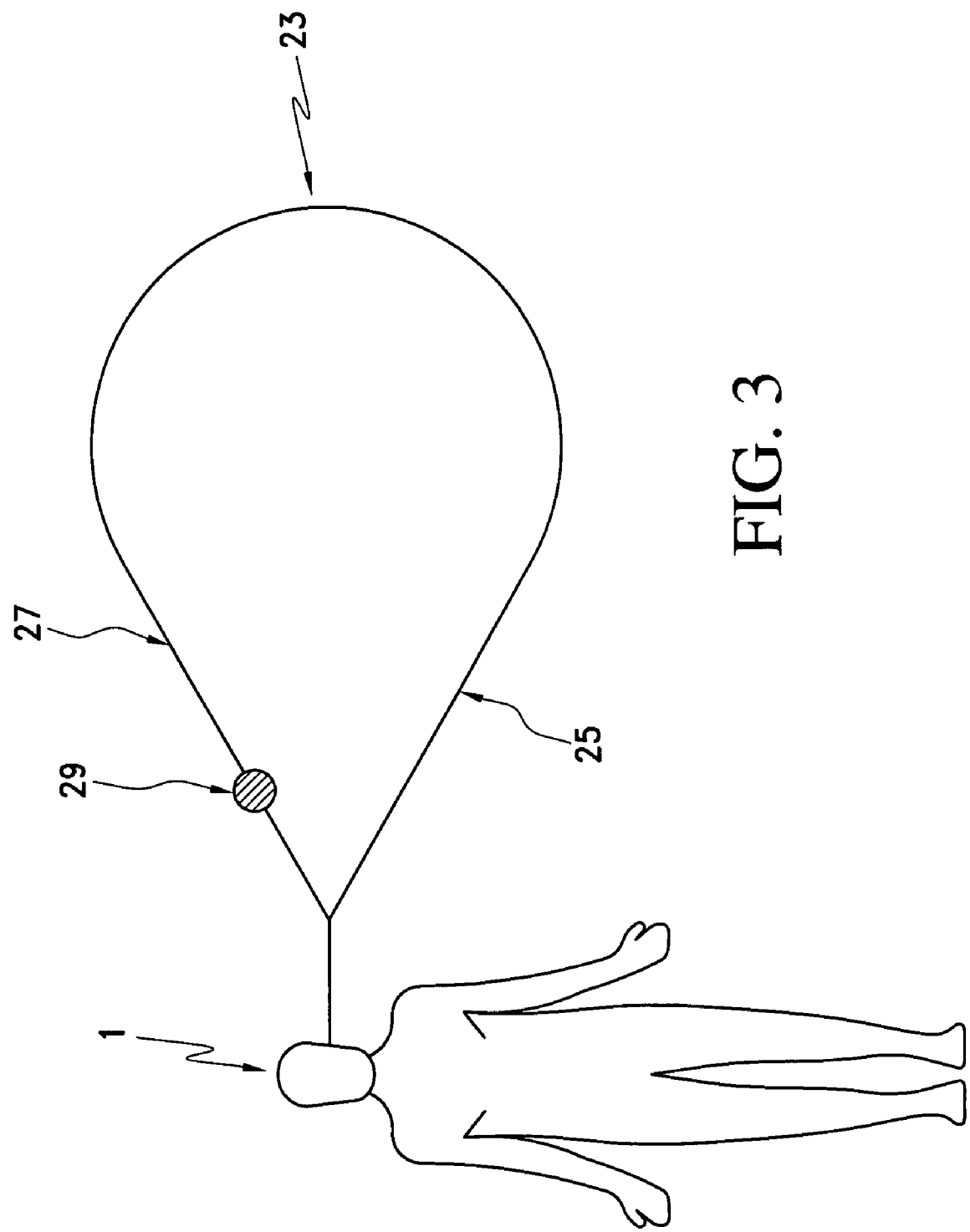
FIG. 3 is a schematic of an arrangement of a medication absorber in the breathing circuit of a patient; and, FIG. 4 is a schematic showing the arrangement of the invention for monitoring an administration of a medication which includes a measuring unit for determining the depth of anesthesia.

FIG. 3 shows again the patient 1 as well as a schematic representation of the breathing circuit 23 with an expiration branch 25 and an inspiration branch 27. A medication absorber is indicated in FIG. 3 by reference numeral 29 and this medication absorber is inserted into the inspiration branch 27 of the breathing circuit 23 for measuring.

The present invention shows for the first time an arrangement for monitoring a dosing of at least one medication administered to a patient. The concentration of an active substance of the medication, which is measured in the breathing gas of a patient, is matched to a computed concentration in the breathing gas. When the administered quantity of the medication is changed, the concentration range is adapted wherein the concentration of the medication measured in the breathing gas corresponds to that which was computed.

A unit for changing the quantity of the medication to be administered to the patient to ensure that the concentration of the medication remains within the concentration range 13 can be an electronic circuit 38 within the evaluation unit 7 which outputs a signal to the device 5 for automatically administering the medication to maintain the medication in the concentration range 13 or, on the other hand, the function of this electronic circuit 38 can be performed manually by an attending physician who could close the loop by observing the display device 34 connected to the evaluation unit 7 or by responding to a warning signal issued by the evaluation unit to the warning device 32.

Figure 4:
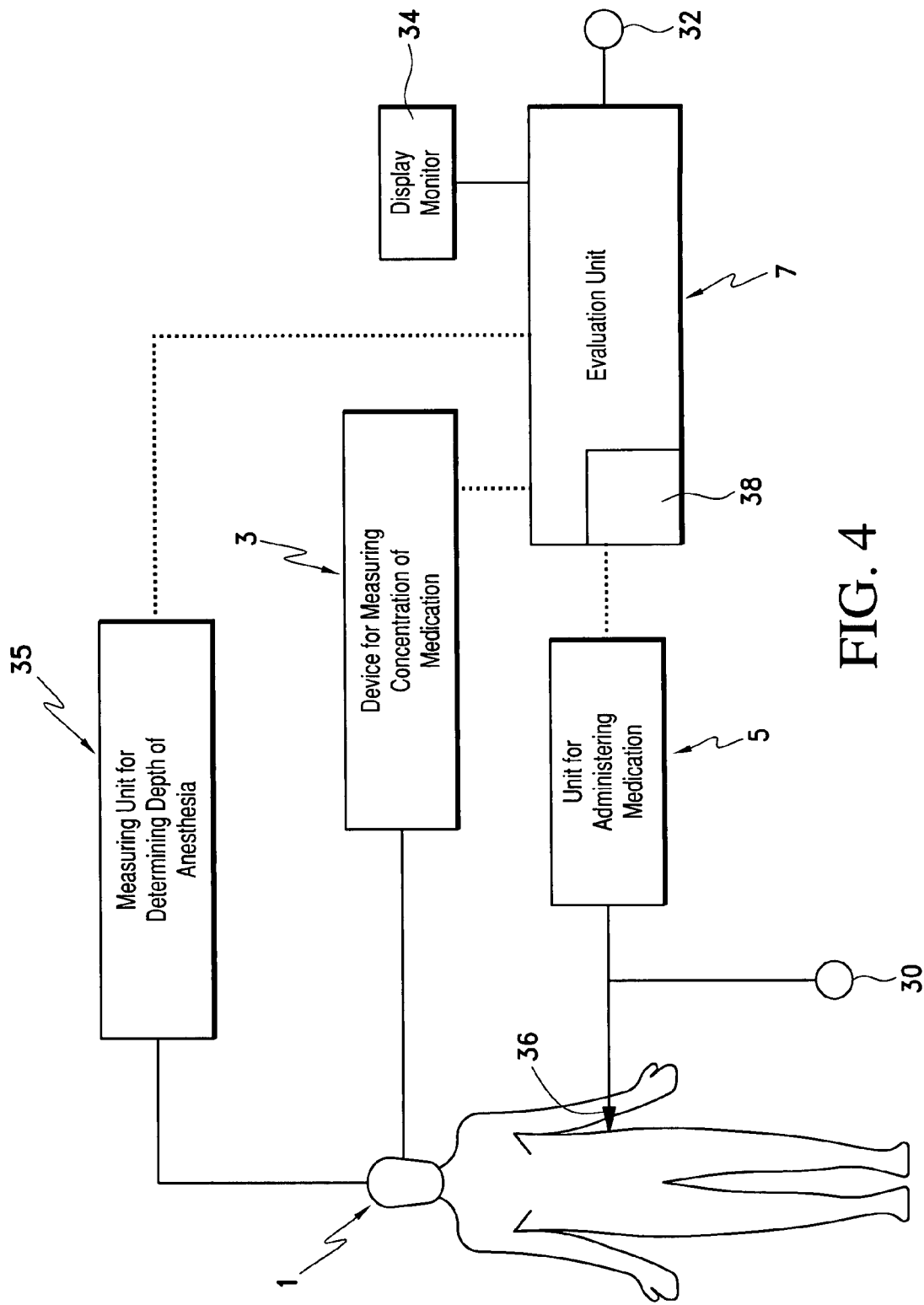

FIG. 4 shows the monitoring arrangement of the invention equipped with a measuring unit 35 for determining the depth of anesthesia. The measuring unit 35 determines the depth of anesthesia, for example, by processing EEG signals obtained from the patient. The monitoring arrangement of FIG. 4 also includes a device 3 for measuring the concentration of the medication in the breathing gas of the patient and a device 5 for administering the medication. If changes in the administration of the medication are set by the user, the evaluation unit 7 will generate an alarm via alarm 32 if signals from measuring unit 35 and the device 3 for measuring the concentration of the medication do not correspond to these changes in medication.

From the foregoing, it can be seen that a basic idea of the invention is also to maintain the flow of medication to the patient so that the medication measured by device 3 of FIG. 1 always remains within the concentration range 13 throughout a surgical procedure to compensate for a leak or other malfunction. This is necessary because it would be impractical to have service personnel make repairs at such a critical time.

The invention further provides an apparatus for administering at least one medication and a method for monitoring a metering of the medication as well as a method for treating a patient.

It is understood that the foregoing description is that of the preferred embodiments of the invention and that various changes and modifications may be made thereto without departing from the spirit and scope of the invention as defined in the appended claims.

What is claimed is:

1. An arrangement for monitoring a dosing of a medication administered to a patient, the arrangement comprising:

an apparatus for administering the medication to said patient;

said apparatus including a device for detecting the quantity of said medication delivered to said patient;

a device for measuring the concentration of said medication in the breathing gas of said patient;

an evaluation unit for detecting a deviation of the concentration of said medication measured in said breathing gas from a first concentration range having upper and lower limits and being narrower than a second concentration range adjustable by an operator or by said evaluation unit;

said evaluation unit being adapted to determine the upper and lower limits of said first concentration range in accordance with a pharmacokinetic model based on the quantity of said medication delivered to the patient; and, an alarm unit connected to said evaluation unit for outputting an alarm announcement when said concentration of said medication measured in said breathing gas passes out of said first concentration range thereby providing an indication of a possible malfunction in said arrangement earlier than when said concentration passes out of said second concentration range.

2. The arrangement of claim 1, further comprising a unit for intravenously administering said medication to the patient.

3. The arrangement of claim 1, wherein the following are included in the monitoring of said dosing: changes measured in an electroencephalogram (EEG); bispectralindex-monitoring (BIS); and, acoustically evoked potentials.

4. The arrangement of claim 1, further comprising a measuring unit for determining the depth of anesthesia of the patient; and, said measuring unit being operatively connected to said evaluation unit.

5. The arrangement of claim 4, wherein said measuring unit processes EEG signals obtained from the patient.

6. The arrangement of claim 1, wherein said breathing gas flows in a breathing circuit having an inspiration branch; and, said arrangement further comprises a medication absorber disposed in said inspiration branch.

7. A method for monitoring a dosing of a medication to a patient utilizing an arrangement for monitoring said dosing, the method comprising the steps of:

administering said medication to said patient;

detecting the quantity of said medication delivered to said patient;

measuring the concentration of said medication in the breathing gas of said patient;

providing a first concentration range for said medication measured in said breathing gas in accordance with a pharmacokinetic model based on the quantity of said medication delivered to said patient;

detecting a deviation of said concentration of said medication measured in said breathing gas from said first concentration range narrower than a second concentration range adjustable by an operator; and, outputting an alarm announcement when said concentration of said medication measured in said breathing gas passes out of said first construction range thereby providing an indication of a possible malfunction in said arrangement earlier than when said concentration passes out of said second concentration range.

8. The method of claim 7, comprising the further step of administering said medication to the patient intravenously.

9. The method of claim 8, comprising the further steps of:

administering said medication in the form of a bolus injection;

determining the blood concentration of said medication with pharmacokinetic computations; and, bringing the computed blood concentration into relationship with the concentration measured in the breathing gas for an improved control.

* * * * *